United States Patent
Weidauer et al.

(10) Patent No.: US 10,806,018 B2
(45) Date of Patent: Oct. 13, 2020

(54) APPARATUS FOR GENERATING ACCELERATED ELECTRONS

(71) Applicant: Fraunhofer-Gesellschaft zur Förderung der angewandten Forschung e.V., Munich (DE)

(72) Inventors: André Weidauer, Dresden (DE); Frank-Holm Rögner, Dresden (DE); Gösta Mattausch, Ullersdorf (DE); Ralf Blüthner, Radebeul (DE); Ignacio Gabriel Vicente Gabas, Dresden (DE); Jörg Kubusch, Dresden (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 16/488,867

(22) PCT Filed: Mar. 2, 2018

(86) PCT No.: PCT/EP2018/055163
§ 371 (c)(1),
(2) Date: Aug. 26, 2019

(87) PCT Pub. No.: WO2018/158422
PCT Pub. Date: Sep. 7, 2018

(65) Prior Publication Data
US 2019/0387605 A1    Dec. 19, 2019

(30) Foreign Application Priority Data
Mar. 3, 2017   (DE) .................. 10 2017 104 509

(51) Int. Cl.
*H05H 1/54* (2006.01)

(52) U.S. Cl.
CPC ..................... *H05H 1/54* (2013.01)

(58) Field of Classification Search
CPC ........................................... H05H 1/54
See application file for complete search history.

(56) References Cited

U.S. PATENT DOCUMENTS

| 3,270,233 A | 8/1966 | Dietrich |
| 3,518,479 A | 6/1970 | Pinsely |
| (Continued) | | |

FOREIGN PATENT DOCUMENTS

| DE | 199 42 142 A1 | 3/2001 |
| DE | 10 2006 012 666 A1 | 9/2007 |
| (Continued) | | |

OTHER PUBLICATIONS

International Search Report, issued in International Application No. PCT/EP2018/055163, dated Jun. 8, 2018, pp. 1-3, European Patent Office, Rijswijk, Netherlands.

*Primary Examiner* — Amy Cohen Johnson
*Assistant Examiner* — Jianzi Chen
(74) *Attorney, Agent, or Firm* — Brinks Gilson & Lione

(57) ABSTRACT

An apparatus is provided for generating accelerated electrons, including a housing; an inlet for supplying a working gas; at least one first cathode; and at least one first anode, between which a corona discharge plasma can be generated. Ions from the corona discharge plasma can be accelerated onto the surface of a second cathode. Electrons emitted by the second cathode can be accelerated in the direction of the electron exit window by means of a second electric voltage applied between the second cathode and a second anode. The housing, the second cathode, and the electron exit window are ring-shaped. The ring-shaped space is divided into ring segments. Each ring segment has at least one wire-shaped electrode, which extends through the ring segment. At least one separate power supply device is associ- (Continued)

ated with each ring segment, by means of which the strength of the electrical current is adjustable.

8 Claims, 2 Drawing Sheets

(56) References Cited

U.S. PATENT DOCUMENTS

| | | |
|---|---|---|
| 3,566,175 A | 2/1971 | Baldwin |
| 8,178,858 B2 | 5/2012 | Bartel et al. |
| 2013/0162134 A1* | 6/2013 | Mattausch ............ H01J 37/075 313/33 |
| 2016/0374261 A1* | 12/2016 | Rogner .................... A01C 1/08 422/186.05 |

FOREIGN PATENT DOCUMENTS

| | | |
|---|---|---|
| DE | 10 2013 111 650 B3 | 2/2015 |
| EP | 0 231 094 A2 | 8/1987 |
| EP | 1 088 797 A1 | 4/2001 |
| WO | WO 2007/107331 A1 | 9/2007 |

* cited by examiner

APPARATUS FOR GENERATING ACCELERATED ELECTRONS

CROSS-REFERENCE TO RELATED APPLICATIONS

This application is a 371 nationalization of international patent application PCT/EP2018/055163 filed Mar. 2, 2018, which claims priority under 35 USC § 119 to German patent application 102017104509.0 filed Mar. 3, 2017. The entire contents of each of the above-identified applications are hereby incorporated by reference.

BACKGROUND

Electron beam technology has been used for several decades on an industrial scale for modifying chemical materials as well as for disinfecting or, more specifically, sterilizing surfaces. The treatment of products can be carried out at atmospheric pressure in a manner that is economically advantageous, for which purpose the electrons are released first in a vacuum, then accelerated and finally have to be decoupled by means of a beam exit window, usually a thin metal foil, into the treatment zone. In order to pass through a sufficiently robust electron exit window, which can be used for large scale industrial application, as well as to ensure a sufficient treatment depth in the product, acceleration voltages of >100 kV are typically required.

Various methods and beam sources are well-established for surface treatment of flat products, such as sheets and strips, while the treatment on all of the sides of shaped bodies, bulk materials and fluids still causes problems. For example, the uniform exposure of curved surfaces to electrons on all sides is geometrically problematic due to shading effects, variable absorption of electron energy on the gas path, and dose inhomogeneities due to the different projection conditions.

With the already existing source systems, such as axial emitters with a fast deflection unit or strip emitters with an elongated cathode, both embodiments of which are operated with a heated thermionic cathode, it is possible to treat a product on all sides, using additional means or with a great deal of equipment and/or technological complexity, only with considerable difficulty. Moreover, electron beam sources, based on thermionic emitters, are also mechanically complicated, difficult to scale and require expensive high voltage power supplies and high vacuum systems. Damage to the beam exit window with the resulting collapse of the vacuum leads to irreversible damage to the cathode system and thus to a high maintenance cost.

DE 199 42 142 A1 discloses an apparatus in which the bulk material is guided past an electron beam device in a free fall several times and bombarded with accelerated electrons. Due to the multiple runs, combined with mixing the bulk material in-between, the probability in this embodiment is very high that the particles of the bulk material are exposed on all sides to accelerated electrons. However, the multiple runs require a considerable amount of time in the course of carrying out the treatment process. In addition, the drawback in this case is that the apparatus is unsuitable for the treatment of larger shaped parts.

DE 10 2006 012 666 A1 offers another solution, which comprises three axial emitters with associated deflection control and three respective electron exit windows. The three electron exit windows are arranged in such a way that they completely encompass a triangular free space. If a substrate is guided through this free space, then the cross section of said substrate can be fully exposed to accelerated electrons in one treatment run. However, if the substrate does not have the same triangular cross section as the free space, enclosed by the three electron exit windows, then the distribution of the dose of exposure of the surface of the substrate to the accelerated electrons will not be homogeneous. The amount of equipment required for this embodiment is also very high, so that this solution is also very expensive.

From WO 2007/107331 A1, an apparatus is known in which only two area beam generators are needed, between which a shaped part moves through for the purpose of sterilizing its surface and can be exposed to accelerated electrons in the meantime. This apparatus also has a plurality of gold reflectors, which are used to reflect marginal rays, emitted from the area beam generators, onto those surface regions of the shaped part that are not in the immediate area of action of the area beam generators. Because the reflectors known from this document are made of pure gold, such apparatuses are also very expensive and thus have an adverse impact on their cost effectiveness. Because reflected electrons have less energy than non-reflected electrons, even with this apparatus only an inhomogeneous energy input into a substrate is possible.

A ring-shaped apparatus for generating accelerated electrons is disclosed in DE 10 201 3 111 650 B3, in which all of the essential components, such as cathode, anode and electron exit window, are designed in a ring shape, so that a ring-shaped electron beam in which the accelerated electrons move towards the interior of the ring can be formed with such an apparatus. For example, strand-shaped substrates, which are moved through the ring opening of the apparatus, can be fully exposed, with respect to the substrate cross section, to accelerated electrons by means of such an apparatus. An apparatus known from DE 10 201 3 111 650 B3 usually has a circular ring shape but can also be designed in any other ring shape. In many applications, it is advantageous if all of the surface regions of a substrate are exposed always with the same energy dose, if possible. In the known apparatuses, such a requirement can be achieved by adapting the cross section of the ring to the cross section of the strand of the strand-shaped substrate to be irradiated when manufacturing the ring-shaped source of radiation. The drawback in this case has the effect that once a ring-shaped radiation source has been manufactured, said radiation source is optimally suitable only for the use of substrates of one type of cross-sectional shape.

DETAILED DESCRIPTION

The invention relates to an apparatus for generating accelerated electrons. In particular, a substrate can be completely exposed to accelerated electrons in a substrate cross section in one treatment run with an apparatus of the present invention. An apparatus in accordance with the invention can be used advantageously when exposing strand-shaped substrates, shaped parts and fluids to accelerated electrons.

Therefore, the invention is based on the technical problem of providing an apparatus that is intended for generating accelerated electrons and by means of which the disadvantages of the prior art can be overcome. In particular, the apparatus is used to satisfy the objective that substrates and, in particular, also strand-shaped substrates of different strand cross sections can be completely exposed to accelerated electrons and in terms of the surface, with respect to the substrate, to an electron density that is as uniform as possible.

One feature of an apparatus in accordance with the present invention is that it is designed so as to be ring shaped; and the electrons can be accelerated in the direction of the ring interior. In this way, a substrate guided through the ring interior of the apparatus can be completely exposed, with respect to a substrate cross section, to accelerated electrons in one irradiation run. At this point, it should be explicitly pointed out that the term "ring-shaped" in the context of the invention is not limited to just a ring in circular shape in all of the ring-shaped apparatuses and components described below, but rather that the term "ring-shaped" in the context of the invention refers only to a loop-shaped, self-contained object, wherein the loop-shaped, self-contained object completely encloses a free space in its cross section, and wherein a substrate can be passed through this free space in the interior of the ring. Although the cross section of the free space, with said cross section being completely enclosed by a ring, is designed in a preferred embodiment of the invention in such a way that said cross section is circular, it can also have any other geometric shape in the broadest sense of the invention.

The invention is explained in more detail below with reference to one exemplary embodiment.

In order to better understand the invention, the terms "ring cylinder" and "ring disk" are also defined at this point with respect to a ring-shaped object. If the inside radius of a circular ring is subtracted from its outside radius, then the result is a measure. If this measure is less than the extension of the ring in the direction of its ring axis, then the ring is designed as a ring cylinder. However, if this measure is greater than the extension of the ring in the direction of its ring axis, then the ring is designed as a ring disk.

Figure 1:
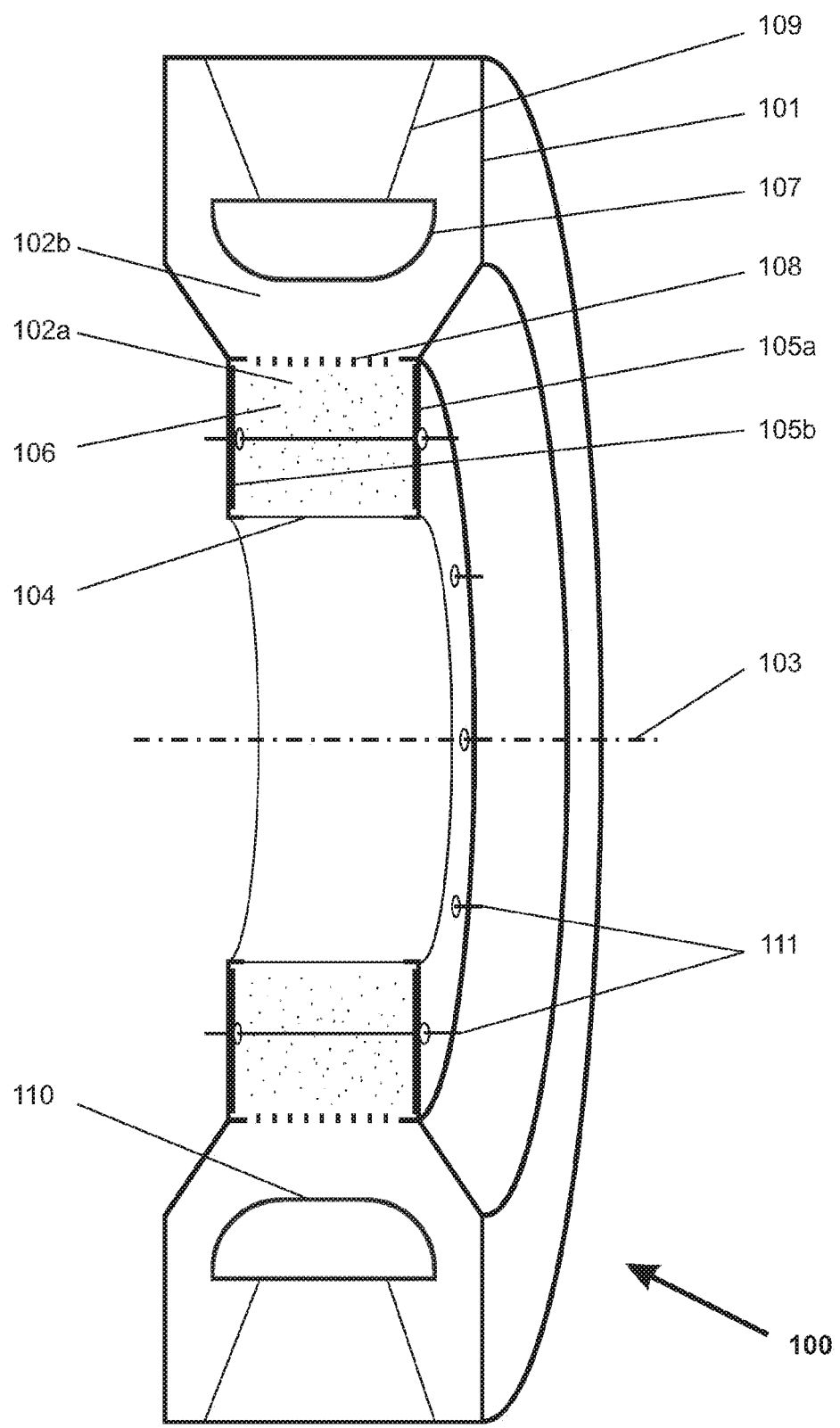
FIG. 1 shows, in schematic form, a perspective cross-sectional view of an apparatus in accordance with the invention.
Figure 2:
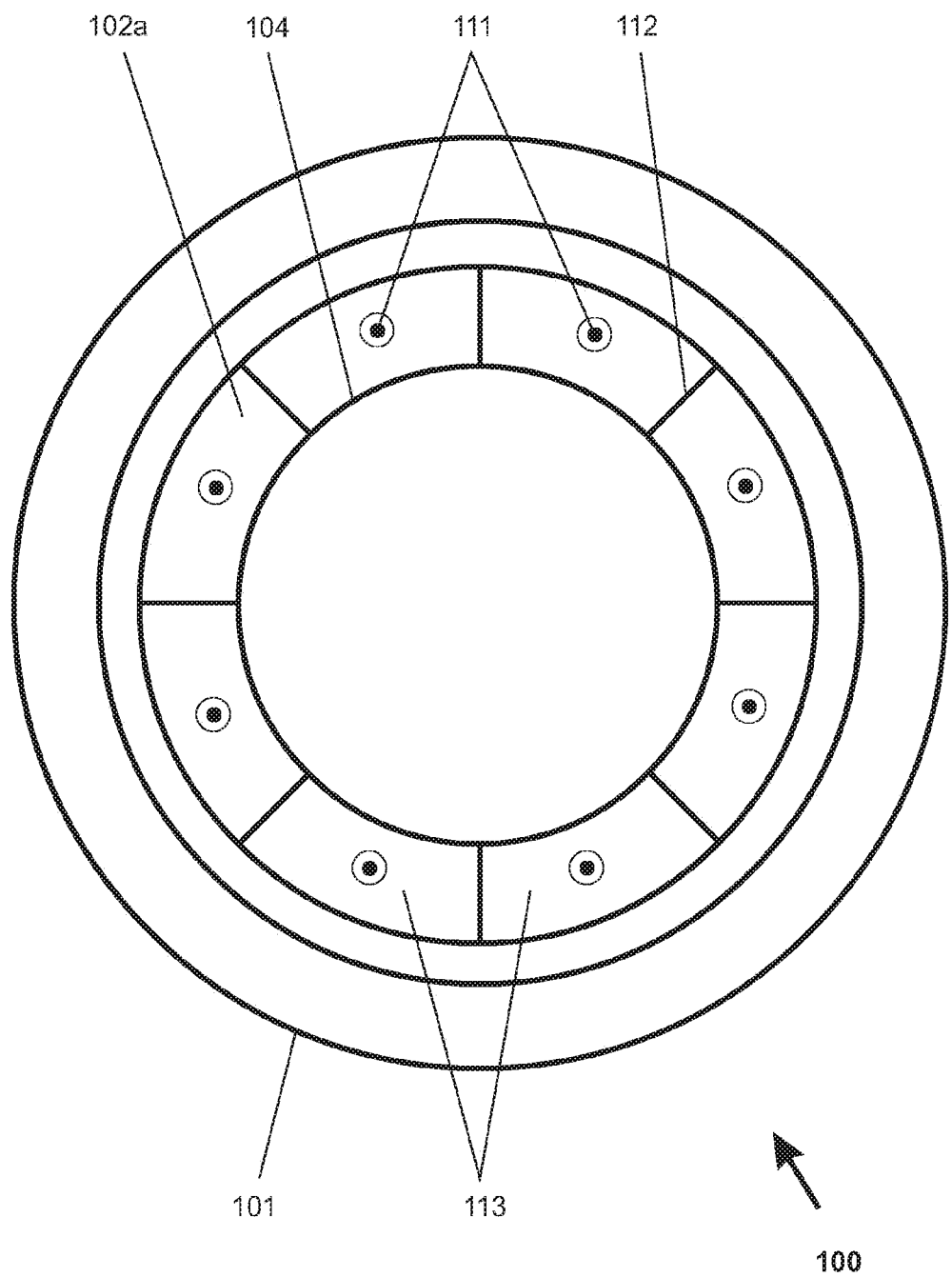
FIG. 2 shows a schematic representation of a plan view of the ring-shaped apparatus from FIG. 1.

In FIG. 1 and FIG. 2 an identical apparatus 100 of the present invention is shown in schematic form: in FIG. 1 as a perspective cross-sectional view and in FIG. 2 as a plan view.

An apparatus in accordance with the invention comprises first a ring-shaped housing 101, which delimits an evacuable space 102 in at least one area, and said evacuable space is divided into the evacuable spaces 102a and 102b. This evacuable space 102 is also ring shaped due to the shape of the housing. In the exemplary embodiment from FIG. 1, the housing 101 is designed so as to be radially symmetrically about a ring axis 103. All of the components that are described below, that are associated with the apparatus 100 and that are referred to as ring shaped are also radially symmetrical and have one and the same ring axis 103. On the inner ring side of the housing 101, the housing 101 is designed as an electron exit window 104 in the shape of a ring cylinder. That means that, when viewed in the exit direction of the electrons, the electron exit window 104 has a surface perpendicular, which is oriented towards the ring interior and in the case of a circular ring cylinder, as in the case of the electron exit window 104, towards the ring axis 103. A working gas is admitted into the evacuable space 102 by means of at least one inlet (not shown in FIG. 1) in the housing 101; and a vacuum is maintained in the range of 0.1 Pa to 20 Pa and preferably in the range of 1 Pa to 3 Pa in the evacuable space 102 by means of at least one pumping means, which is also not shown in FIG. 1.

Furthermore, an apparatus in accordance with the invention comprises at least one first cathode and at least one first anode, between which a corona discharge plasma can be generated in the evacuable space 102 by means of a first applicable electric voltage that is provided by a first power supply means. In the exemplary embodiment, two wall regions of the housing 101, where said wall regions are formed as a ring disk, are designed as the first cathodes 105a and 105b, which are opposite one another and thus delimit the space 102a. Therefore, in the case of the apparatus 100 the housing 101 and the first cathodes 105a, 105b have the same electric potential that at the same time is the electric ground potential of the apparatus 100.

The first anode of an apparatus in accordance with the invention is designed as a number of wire-shaped electrodes that extend through the space 102a and, in the case of a housing in the shape of a circular ring such as the housing 101, are arranged preferably on an identical radius and at the same distant from one another around the axis 103. In this case, the wire-shaped electrodes 111, which may have a slightly positive voltage potential in a range of +0.25 kV to +5.0 kV with respect to the housing 101, are passed in an electrically insulated manner through the housing 101 and the first cathodes 105a 105b. Due to the electric voltage applied between the wire-shaped electrodes 111 and the first cathodes 105a and 105b, a plasma is formed in the space 102a. Therefore, the space 102a is also referred to below as the plasma space 102a.

Furthermore, an apparatus in accordance with the invention comprises at least one second cathode and at least one second anode, between which a second electric voltage is switched by means of a second power supply means. In the case of the apparatus 100, a ring-shaped cathode 107 is designed as a second cathode; and a ring-shaped and simultaneously lattice-shaped anode 108 is designed as a second anode.

In an apparatus in accordance with the invention, the second cathode represents the cathode for emitting secondary electrons, which are subsequently accelerated; and for this purpose said second cathode has an electric high voltage potential, preferably in the range from −100 kV to −300 kV. The second cathode 107 is electrically insulated from the housing 101 by means of an insulator 109.

In the embodiment of the invention described in FIG. 1, the second anode 108 and the first cathodes 105a, 105b have the same electric potential, which is designed as an electric ground potential. As an alternative, the second anode and the first cathode may also have different electric potentials.

Out of the plasma 106 in the space 102a, ions are accelerated through the lattice-shaped second anode 108 in the direction of the second cathode 107 by applying a high voltage potential in the range of −100 kV to −300 kV. At said second cathode, the ions impinge on a surface region 110 of the second cathode 107, the surface perpendicular of which is oriented towards the ring interior of the housing and in the case of a radially symmetrical housing, such as the housing 101, is oriented towards the ring axis 103. When the ions impinge on the surface region 110, the ions thus have a potential differential that largely corresponds to the acceleration voltage of the apparatus 100. Upon impact, the energy of the ions is released in a very thin surface layer of the cathode 107 in the surface region 110, a state that results in the release of secondary electrons. In the case of the aforementioned electric voltages at the second cathode 107, the ratio between released electrons and impinging ions is on the order of 10, an aspect that makes this manner of generating accelerated electrons very efficient. The resulting secondary electrons are greatly accelerated by the applied electric field and fly through the lattice-shaped anode 108, which is designed in the shape of a ring-shaped cylinder, and the plasma 106 in the space 102a. After having crossed the electron exit window 104, which may be designed, for example, as a thin metal foil, the electrons push into the free space, enclosed by the ring-shaped housing 101, in which there may be a higher pressure than in the space 102 and can be guided through a substrate, which is to be exposed to electrons, through the ring opening of the housing. Materials that may be used for the electron exit window 104 include all materials, which are known from the prior art for an electron exit window, such as titanium. In addition, it is advantageous for the purpose of a higher mechanical stability of the electron exit window 104 to provide said electron exit window with a support grid, which is also known from the prior art.

Owing to the ring-shaped design of all of the aforementioned components of an apparatus in accordance with the invention, a self-contained, ring-shaped strip of accelerated electrons is generated with said apparatus, wherein the direction of movement of the accelerated electrons is oriented in relation to the free space, enclosed by the housing ring. The free space, which is enclosed by the housing ring and through which a substrate can be passed, is also referred to below as the treatment space. In the case of a radially symmetrical apparatus of the present invention, such as the apparatus 100, the direction of movement of the accelerated electrons is preferably oriented in relation to the ring axis 103. As a result, a substrate guided through the ring interior of the housing of an apparatus in accordance with the invention can be fully exposed with respect to a substrate cross section to accelerated electrons in one run. Therefore, an apparatus in accordance with the invention is particularly suitable for exposing strand-like substrates of shaped parts but also of fluids to accelerated electrons.

For the sake of completeness, it should be mentioned at this point that an apparatus in accordance with the invention also comprises a means for cooling the apparatus, a feature that is also known from the prior art even in the case of apparatuses for generating accelerated electrons. Thus, this means for cooling an apparatus of the present invention comprises, for example, cooling ducts that extend within the insulator 109 and through which a cooling medium flows.

The second anode 108, which is preferably designed as a lattice-shaped ring cylinder and which represents the spatial boundary between the evacuable spaces 102a and 102b in an apparatus of the present invention, fulfills three essential tasks. On the one hand, said second anode causes an acceleration of the ions, extracted from the plasma, in the direction of the second cathode due to the voltage differential between said second anode and the second cathode 107. On the other hand, said second anode also causes an acceleration of the secondary electrons, generated by the ion bombardment, in the direction of the electron exit window 104. Due to the fact that the ring-shaped lattice structure of the second anode 108 is designed parallel to the secondary electron-emitting surface 110 of the second cathode 107, an electric field is formed in such a way that the paths of the accelerated secondary electrons run largely parallel. Furthermore, the second anode 108 shields the plasma from the voltage potential of the second cathode 107 and, in so doing, prevents too many ions from drifting in the direction of the second cathode 107 and thus helps to maintain the plasma 106 in the space 102a.

In an apparatus of the present invention, the ring-shaped plasma space 102a is divided, as can be seen in FIG. 2, into ring segments 113 by means of walls 112. In the case of the apparatus 100, the walls 112 are made of an electrically conductive material and have the same electric voltage potential as the housing 101, the first cathodes 105a, 105b and also the electron exit window 104. In the exemplary embodiment this electric voltage potential is the electric ground potential. In this context, each ring segment 113 comprises at least one wire-shaped electrode 111, which extends through the ring segment 113, preferably parallel to the ring axis 103. Furthermore, each ring segment 113 is allocated a separate power supply means (not shown in the figures), by means of which the strength of the electric current, which flows through the at least one electrode 111 of a respective ring segment 113, is adjustable.

Because of the voltage potential conditions described above, the first cathodes 105a, 105b, the associated walls 112 as well as a respective section of the electron exit window 104 in the apparatus 100 act as a cathode for the plasma discharge within a respective ring segment 113.

The division of the ring-shaped plasma space 102a into ring segments 113 in interaction with the separate control of the strength of the current, which flows through the at least one wire-shaped electrode 111 of a ring segment 113, makes it possible for a separate plasma to be formed with a separate plasma thickness within each ring segment 113. As a result, the amount of electrons emitted via that surface section of the electron exit window 104 that is associated with a respective ring segment 113 is separately adjustable for each ring segment 113. Consequently the ring-shaped emission profile of an apparatus of the present invention can be adapted to the contour of the cross-sectional area or, more specifically, to the different dose requirements of individual surface regions of a substrate to be exposed to accelerated electrons. If the walls 112 of an apparatus of the present invention are integrated in the apparatus by means of an assembly variant that can be removed, a further adaptation to the substrate profiles can be achieved by displacing the walls 112 and/or by changing the number of walls 112 used in interaction with the altered control of the wire-shaped electrodes, which are then part of a ring segment, without having to immediately manufacture a totally new beam apparatus.

In the apparatus 100 shown in FIGS. 1 and 2, the ring-shaped plasma space 102a is divided into 8 ring segments 113 of equal size merely for illustrative purposes. As an alternative, the plasma space 102a of an apparatus in accordance with the invention can also be subdivided into any desired number of ring segments, the size of which may also vary with respect to the ring angle. Also, the number of wire-shaped electrodes 111 per ring segment 113 is selected merely as an example. As an alternative, the ring segments of an apparatus in accordance with the invention may also comprise more than just one wire-shaped electrode.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. An apparatus for generating accelerated electrons, said apparatus comprising:
a housing configured to delimit an evacuable space, the housing including an electron exit window;
an inlet configured to feed a working gas into the evacuable space;
a first cathode;
a first anode designed as a number of wire-shaped electrodes that extend through the evacuable space, wherein a corona discharge plasma can be generated in the evacuable space between the first cathode and first anode by means of a first applicable electric voltage;
a second cathode, the second cathode including a surface region, wherein ions from the corona discharge plasma can be accelerated onto the surface of the second cathode; and
a second anode, wherein electrons, emitted from the second cathode, can be accelerated in the direction of the electron exit window of the housing by a second electric voltage applied between the second cathode and the second anode,
wherein the housing, the second cathode, and the electron exit window are ring shaped,
wherein the surface perpendiculars of the electron exit window (104) and of the surface region of the second cathode, from which electrons can be emitted, are oriented towards the ring interior of the ring-shaped housing;
wherein the ring-shaped space is divided into ring segments by walls, wherein each ring segment has at least one of the wire-shaped electrodes of the first anode, each of the at least one of the wire-shaped electrodes extends through the ring segment;
and wherein each ring segment is allocated at least one separate power supply, by means of which a strength of an electric current, which flows through the at least one of the wire-shaped electrodes of a respective ring segment, is adjustable.

2. The apparatus according to claim 1, wherein the walls are made of an electrically conductive material.

3. The apparatus according to claim 2, wherein the walls have the same electric potential as the housing.

4. The apparatus according to claim 3, wherein the walls have electric ground potential.

5. The apparatus according to claim 1, wherein the housing and the first cathode have the same electric potential.

6. The apparatus according to claim 1, wherein the housing and the second anode have the same electric voltage potential.

7. The apparatus according to claim 1, wherein the second anode is designed as a lattice-shaped ring cylinder.

8. The apparatus according to claim 1, wherein the wire-shaped electrodes are arranged on an identical radius and at the same distance from one another around the ring axis of the housing.

* * * * *